(12) United States Patent
Ikeuchi et al.

(10) Patent No.: US 10,941,192 B2
(45) Date of Patent: Mar. 9, 2021

(54) VHH ANTIBODY

(71) Applicant: Panasonic Intellectual Property Management Co., Ltd., Osaka (JP)

(72) Inventors: Emina Ikeuchi, Tokyo (JP); Jin Muraoka, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/372,506

(22) Filed: Apr. 2, 2019

(65) Prior Publication Data

US 2019/0375824 A1 Dec. 12, 2019

(30) Foreign Application Priority Data

Jun. 8, 2018 (JP) ................................ 2018-110552

(51) Int. Cl.
*C07K 16/06* (2006.01)
*C12N 15/85* (2006.01)

(52) U.S. Cl.
CPC ............ *C07K 16/065* (2013.01); *C12N 15/85* (2013.01); *C07K 2317/51* (2013.01); *C07K 2317/94* (2013.01); *C12N 2015/8518* (2013.01)

(58) Field of Classification Search
CPC .............. C07K 16/065; C07K 2317/94; C07K 2317/51; C07K 2317/569; C07K 2317/92; C07K 16/18; C12N 15/85; C12N 2015/8518

See application file for complete search history.

(56) References Cited

FOREIGN PATENT DOCUMENTS

JP 2014-042515 3/2014

OTHER PUBLICATIONS

Edwards et al,The Remarkable Flexibility of the Human Antibody Repertoire; Isolation of Over One Thousand Different Antibodies to a Single Protein, BLyS,2003,J. Mol. Biol. (2003) 334, 103-118 (Year: 2003).*
Chen et al, Enhancement and destruction of antibody function by somatic mutation: unequal occurrence is controlled by V gene combinatorial associationsThe EMBO Journal vol. 14 No. 1 2 pp. 2784-2794, 1995 (Year: 1995).*
Thomas A. Kunkel et al., "Rapid and Efficient Site-Specific Mutagenesis without Phenotypic Selection", Methods in Enzymology, 154, 350, 367-382 (1987).
Mark J. Zoller et al., "Oligonucleotide-Directed Mutagenesis of DNA Fragments Cloned into M13 Vectors", Methods in Enzymology, 100, 468-500 (1983).
Robert L. Leisinger et al., "A Convenient Method for Stepwise Synthesis of Oligothymidylate Derivatives in Large-Scale Quantities", Journal of the American Chemical Society / 89:18 / Aug. 30, 1967, pp. 4801-4803.
Robert L. Leisinger et al., "Synthesis of Oligothymidylates via Phosphotriester Intermediates", Journal of the American Chemical Society / 91:12 / Jun. 4, 1969, pp. 3350-3355.
S. L. Beaucage et. al., "Deoxynucleoside Phosphoramidites—A New Class of Key Intermediates For Deoxypolynucleotide Synthesis", Tetrahedron Letters, vol. 22, No. 20, pp. 1859-1862 (1981).
L. J. McBride et al., "An Investigation of Several Deoxynucleoside Phosphoramidites Useful For Synthesizing Deoxyoligonucleotides", Tetrahedron Letters, vol. 24, No. 3, 245-248 (1983).
Michiel M. Harmsen et al.,"Llama heavy-chain V regions consist of at least four distinct subfamilies revealing novel sequence features", Molecular Immunology 37, 579-590 (2000).

* cited by examiner

*Primary Examiner* — Amy E Juedes
*Assistant Examiner* — Brian Hartnett
(74) *Attorney, Agent, or Firm* — McDermott Will and Emery LLP

(57) ABSTRACT

Provided is a VHH antibody including an amino acid sequence in which at least one selected from the group consisting of glycine in position 36, arginine in position 50, and glycine in position 78, on the basis of IMGT numbering, of the amino acid sequence represented by SEQ ID NO: 1 is substituted with another amino acid. The VHH antibody according to the present disclosure is thermostable.

1 Claim, 3 Drawing Sheets

Specification includes a Sequence Listing.

VHH ANTIBODY

INCORPORATION BY REFERENCE-SEQUENCE LISTING

The material contained in the ASCII text file named "P1013355US01_ST25.txt" created on Nov. 5, 2018, and having a file size of 15,248 bytes is incorporated by reference herein.

BACKGROUND

1. Technical Field

The present disclosure relates to a thermostable VHH antibody.

2. Description of the Related Art

A VHH antibody is a special antibody, which does not have a light chain. The VHH antibody is found mainly in a serum of an artiodactyl and an animal of the family Camelidae (e.g., a Bactrian camel, an Arabian camel, a llama, an alpaca, a vicuna or a guanaco). The VHH antibody has the lowest molecular weight (e.g., approximately 12-15 kDa) in immunoglobulin fragments each capable of binding to an antigen. In addition, it is relatively easy to express the VHH antibody with *Escherichia coli*. Furthermore, the VHH antibody has relatively high thermal stability. For these reasons, the study of the VHH antibody has been advanced.

The VHH antibody is required to have much higher thermal stability. Patent Literature 1 discloses a technique in which amino acids in positions 57, 82, and 92 of an antibody of the animal of the family Camelidae are substituted to improve the thermal stability thereof. However, it is required to provide more various thermostable VHH antibodies.

CITATION LIST

Patent Literature

Patent Literature 1: Japanese Patent Application Publication No. 2014-042515

SUMMARY

An object of the present disclosure is to provide a thermostable VHH antibody.

The present inventors prepared the VHH antibody represented by SEQ ID NO: 1. Furthermore, the present inventors found that an amino acid in a specific position of the VHH antibody represented by SEQ ID NO: 1 is substituted to provide a VHH antibody having much higher thermal stability.

The present disclosure provides a VHH antibody including the amino acid sequence represented by SEQ ID NO: 1. Furthermore, the present disclosure provides a VHH antibody including the amino acid sequence in which at least one selected from the group consisting of glycine in position 36, arginine in position 50, and glycine in position 78 of the amino acid sequence represented by SEQ ID NO: 1 on the basis of the IMGT numbering is substituted with another amino acid.

The present disclosure provides a thermostable VHH antibody.

DETAILED DESCRIPTION OF THE EMBODIMENT

Figure 1:
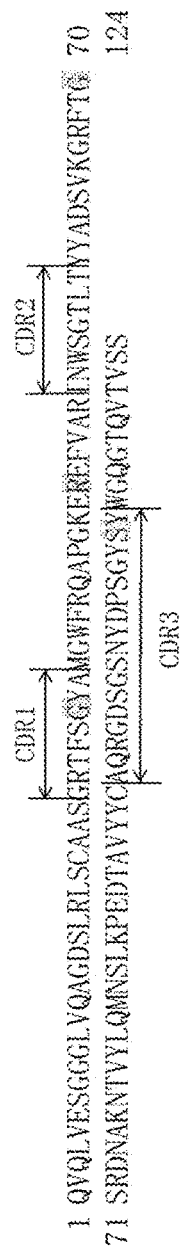
FIG. 1 is a diagram showing the amino acid sequence of SEQ ID NO: 1.

The term "VHH antibody" used in the present specification means a variable region domain of a heavy chain antibody. A typical VHH antibody usually consists of 100-150 amino acid residues, in particular, 115-135 amino acid residues.

The verb "include" used in the present specification includes "consist of" and "essentially consist of".

In the present specification, an acid and an amino acid may be abbreviated on the basis of an abbreviation standardized by IUPAC or used conventionally in the art.

The VHH antibody according to the present embodiment includes the amino acid sequence represented by SEQ ID NO: 1. Alternatively, the VHH antibody according to the present embodiment consists of the amino acid sequence represented by SEQ ID NO: 1.

For numbering amino acid sequences of antibody, the following two numberings are known.

(i) ImMunoGeneTics Database numbering (hereinafter, referred to as "IMGT numbering"); and (ii) Kabat numbering In the present specification, the IMGT numbering is used unless otherwise stated.

The following Table 1 is a table in which the sequence of SEQ ID NO: 1 is rewritten in accordance with the IMGT numbering.

TABLE 1

| | IMGT number | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Amino acid | Q | V | Q | L | V | E | S | G | G | — | G | L |

| | IMGT number | | | | | | | | | | | |
|---|---|---|---|---|---|---|---|---|---|---|---|---|
| | 13 | 14 | 15 | 16 | 17 | 18 | 19 | 20 | 21 | 22 | 23 | 24 |
| Amino acid | V | Q | A | G | D | S | L | R | L | S | C | A |

TABLE 1-continued

| IMGT number | 25 | 26 | 27 | 28 | 29 | 30 | 31 | 32 | 33 | 34 | 35 | 36 |
|---|---|---|---|---|---|---|---|---|---|---|---|---|
| Amino acid | A | S | G | R | T | F | — | — | — | — | S | G |

| IMGT number | 37 | 38 | 39 | 40 | 41 | 42 | 43 | 44 | 45 | 46 | 47 | 48 |
|---|---|---|---|---|---|---|---|---|---|---|---|---|
| Amino acid | Y | A | M | G | W | F | R | Q | A | P | G | K |

| IMGT number | 49 | 50 | 51 | 52 | 53 | 54 | 55 | 56 | 57 | 58 | 59 | 60 |
|---|---|---|---|---|---|---|---|---|---|---|---|---|
| Amino acid | E | R | E | F | V | A | R | I | N | W | S | — |

| IMGT number | 61 | 62 | 63 | 64 | 65 | 66 | 67 | 68 | 69 | 70 | 71 | 72 |
|---|---|---|---|---|---|---|---|---|---|---|---|---|
| Amino acid | — | G | T | L | T | Y | Y | A | D | S | V | K |

| IMGT number | 73 | 74 | 75 | 76 | 77 | 78 | 79 | 80 | 81 | 82 | 83 | 84 |
|---|---|---|---|---|---|---|---|---|---|---|---|---|
| Amino acid | — | G | R | F | T | G | S | R | D | N | A | K |

| IMGT number | 85 | 86 | 87 | 88 | 89 | 90 | 91 | 92 | 93 | 94 | 95 | 96 |
|---|---|---|---|---|---|---|---|---|---|---|---|---|
| Amino acid | N | T | V | Y | L | Q | M | N | S | L | K | P |

| IMGT number | 97 | 98 | 99 | 100 | 101 | 102 | 103 | 104 | 105 | 106 | 107 | 108 |
|---|---|---|---|---|---|---|---|---|---|---|---|---|
| Amino acid | E | D | T | A | V | Y | Y | C | A | Q | R | G |

| IMGT number | 109 | 110 | 111 | 111A | 111B | 112B | 112A | 112 | 113 | 114 | 115 | 116 |
|---|---|---|---|---|---|---|---|---|---|---|---|---|
| Amino acid | D | S | G | S | N | Y | D | P | S | G | Y | S |

| IMGT number | 117 | 118 | 119 | 120 | 121 | 122 | 123 | 124 | 125 | 126 | 127 | 128 |
|---|---|---|---|---|---|---|---|---|---|---|---|---|
| Amino acid | Y | W | G | Q | G | T | Q | V | T | V | S | S |

The present disclosure provides a VHH antibody including or consisting of an amino acid sequence in which at least one selected from the group consisting of glycine in position 36, arginine in position 50, and glycine in position 78, on the basis of the IMGT numbering, of the amino acid sequence represented by SEQ ID NO: 1 is substituted with another amino acid. Serine in position 116 of the amino acid sequence represented by SEQ ID NO: 1 may be substituted with another amino acid.

Pursuant to the numbering described in M. M. Harmsen et al.: Molecular Immunology 37 (2000) 579-590, the positions 36, 50, 78 and 116 of the amino acid sequence of SEQ ID NO: 1 represented on the basis of the IMGT numberings are positions 32, 50, 78, and 133 of amino acid sequence, respectively.

Glycine in position 36 is substituted with, for example, an acidic or basic amino acid such as aspartic acid, glutaminic acid, arginine, lysin, histidine, asparagine, or glutamine. In particular, glycine in position 36 is substituted with an acidic amino acid such as aspartic acid, glutaminic acid, asparagine, or glutamine, or with a basic amino acid such as arginine, lysin, or histidine. The principle of improvement of thermal stability by the substitution is unclear; however, electrostatic interaction generated between the acidic or basic amino acid and an amino acid located at another position may stabilize the structure of the amino acid sequence.

Arginine in position 50 is substituted with, for example, anon-polar amino acid or an uncharged amino acid such as alanine, valine, leucine, isoleucine, proline, phenylalanine, methionine, tryptophan, cysteine, serine, threonine, asparagine, glutamine or tyrosine. In particular, arginine in position 50 is substituted with a non-polar amino acid such as alanine, valine, leucine, isoleucine, proline, phenylalanine, methionine, tryptophan, or cysteine, or with an amino acid having an aliphatic side chain such as valine, leucine or isoleucine. The principle of improvement of thermal stability by the substitution is unclear; however, an interspace which is generated due to the residue of arginine may be filled due to the substitution with the above-mentioned non-polar or uncharged amino acid.

Glycine in position 78 is substituted with an amino acid having higher volume than glycine. An example of the amino acid having higher volume than glycine is alanine, valine, leucine, isoleucine, proline, phenylalanine, methionine, tryptophan, cysteine, aspartic acid, glutaminic acid, arginine, lysin, histidine, serine, threonine, asparagine, glutamine, or tyrosine. In particular, glycine in position 78 is substituted with a non-polar or uncharged amino acid such as alanine, valine, leucine, isoleucine, proline, phenylalanine, methionine, tryptophan, cysteine, serine, threonine, asparagine, glutamine, or tyrosine; or with a non-polar amino acid such as alanine, valine, leucine, isoleucine, proline, phenylalanine, methionine, tryptophan, or cysteine; or with an amino acid having an aliphatic side chain such as valine, leucine or isoleucine. The principle of improvement of thermal stability by the substitution is unclear; however, an interspace which is not filled with the residue of glycine may be filled due to the substitution with the above-mentioned amino acid, which has a larger volume.

Serine in position 116 is substituted with, for example, an acidic or basic amino acid such as aspartic acid, glutaminic acid, arginine, lysin, histidine, asparagine or glutamine. In particular, serine in position 116 is substituted with an acidic amino acid such as aspartic acid, glutaminic acid, asparagine or glutamine, or with a basic amino acid such as arginine, lysin or histidine. The principle of improvement of thermal stability by the substitution is unclear; however, electrostatic interaction generated between the acidic or basic amino acid and an amino acid located at another position may stabilize the structure of the amino acid sequence, or electrostatic interaction generated between the substituted amino acids in positions 116 and 36 may stabilize the structure of the amino acid sequence. Therefore, glycine in position 36 and serine in position 116 may be substituted with a basic amino acid and an acidic amino acid, respectively. Alternatively, glycine in position 36 and serine in position 116 may be substituted with an acidic amino acid and a basic amino acid, respectively.

The VHH antibody according to the present embodiment has higher denaturation median temperature Tm than the VHH antibody represented by SEQ ID NO: 1. The denaturation median temperature Tm can be measured with a differential scanning calorimeter (hereinafter, referred to as "DSC"). Hereinafter, a method for measuring denaturation median temperature Tm of the VHH antibody according to the present embodiment will be described. First, the VHH antibody according to the present embodiment is dissolved in a phosphate buffered saline (hereinafter, referred to as "PBS") having a pH of 7.4 to provide a mixture solution. Then, the mixture solution is diluted with PBS in such a manner that the VHH antibody according to the present embodiment has a concentration of 60 micromol/liter. Finally, the denaturation median temperature Tm of the mixture solution is measured with DSC.

As one example, the difference between the denaturation median temperature Tm of the VHH antibody according to the present embodiment and the denaturation median temperature Tm of VHH antibody represented by SEQ ID NO: 1 is not less than 1 degree Celsius, not less than 2 degrees Celsius, not less than 3 degrees Celsius, not less than 4 degrees Celsius, not less than 5 degrees Celsius, not less than 6 degrees Celsius, not less than 7 degrees Celsius, not less than 8 degrees Celsius, not less than 9 degrees Celsius, or not less than 10 degrees Celsius. The VHH antibody according to the present embodiment has denaturation median temperature Tm of not less than 50 degrees Celsius (for example, not less than 55 degrees Celsius, not less than 57 degrees Celsius, not less than 59 degrees Celsius, not less than 61 degrees Celsius, not less than 63 degrees Celsius, or not less than 65 degrees Celsius). This means that the VHH antibody according to the present embodiment has thermal stability.

An example of a method for substituting a specific amino acid included in the VHH antibody will be listed below.

(i) Genetic method such as site-specific mutation incorporation (refer to the following literatures)
Methods in Enzymology, 154, 350, 367-382 (1987); and
Methods in Enzymology, 100, 468 (1983);

(ii) Chemically synthetic method such as phosphorus acid triester method or phosphate amidite method (refer to the following literatures)
J. Am. Chem. Soc., 89, 4801 (1967);
J. Am. Chem. Soc., 91, 3350 (1969);
Tetrahedron Lett., 22, 1859 (1981); and
Tetrahedron Lett., 24, 245 (1983).

These methods may be combined.

In particular, a DNA can be synthesized chemically by a phosphoramidite method or a triester method. Alternatively, a DNA can be synthesized with a commercially-available automatic oligonucleotide synthesizer. A double-stranded DNA fragment is provided by synthesizing complimentary strands, and then, annealing the complimentary strands to each other under an appropriate condition. Alternatively, the double-stranded DNA fragment is provided by a polymerase chain reaction method (hereinafter, "PCR method") using appropriate primer sequences and a DNA polymerase from a chemically synthesized single-stranded DNA fragment.

The VHH antibody according to the present embodiment includes or consists of the amino acid sequence represented by any one of SEQ ID NO: 3-SEQ ID NO: 12.

The VHH antibody according to the present embodiment can be provided on the basis of the amino acid sequence thereof in accordance with a known method, for example, by chemical synthesis, purification from animal cells or tissues, or expression using a transfectant containing a polynucleotide coding for the VHH antibody according to the present embodiment. The transfectant is not limited, as long as the transfectant is a cell in which the VHH antibody is expressed from the polynucleotide coding for the VHH antibody. An example of the transfectant is bacteria such as *E. coli*, yeast, a fungus, or a cell such as an insect cell or a mammalian cell.

The VHH antibody according to the present embodiment can be used in an antibody medicine, an immunologic diagnostic agent, an immunologic detection method, a reagent for the experiment, an antibody hybrid material, affinity chromatography, or drug delivery system. The VHH antibody according to the present embodiment may be used in a state of a composite to which another substance has been bound (e.g., a composite to which a solid support or a labeled substance has been bound).

As long as the solid support is a support insoluble in a solvent used for a reaction system of an antigen-antibody reaction, a shape and a material of the solid support is not limited. An example of the shape of the solid support is a plate, a bead, a disk, a tube, a filter, and a film. An example of a material of the solid support is a polymer such as polyethylene terephthalate, cellulose acetate, polycarbonate, polystyrene, or polymethylmethacrylate, a metal such as gold, silver, or aluminum, or glass. An example of a method for binding the antibody to the solid support is physical adsorption method, a covalent binding method, an ion bonding method, or a cross-linking method.

An example of the labeled substance is a fluorescent substance, a luminescent substance, a dye, an enzyme, or a radioactive substance. An example of a method for binding the antibody to the labeled substance is a physical adsorption method, a covalent binding method, an ion bonding method, or a cross-linking method.

In the detection method in which the VHH antibody according to the present invention is used, the composite including the VHH antibody is brought into contact with a test sample. Then, detected is a change of a physical amount based on an antigen-antibody reaction generated between an analyte contained in the test sample and the VHH antibody included in the composite. An example of the physical amount is luminescence intensity, chromaticity, light transmission, turbidity, absorbance, or radiation dose. An example of the detection method is an enzyme immunoassay method, an immunochromatography method, a latex agglutination method, a radioimmunoassay method, a fluorescence immunoassay method, or a surface plasmon resonance spectroscopy method.

A detection device in which the VHH antibody according to the present invention is employed includes a detector for detecting any one of the physical amount which may be changed on the basis of the antigen-antibody reaction. The detector is composed of a known device such as a photometer, a spectroscope, or a dosimeter.

The VHH antibody according to the present embodiment may be used not only as the composite formed by binding to another substance but also as a composition containing the VHH antibody according to the present embodiment or a kid including the VHH antibody according to the present embodiment.

The present disclosure relates to a method for improving thermal stability of the VHH antibody represented by SEQ ID NO: 1. The method comprises a step of substituting at least one selected from the group consisting of glycine in position 36, arginine in position 50, and glycine in position 78 on the basis of the IMGT numbering of the VHH antibody represented by SEQ ID NO: 1 with another amino acid. Furthermore, the method may comprise a step of substituting serine in position 116 on the basis of the IMGT numbering of the VHH antibody represented by SEQ ID NO: 1 with another amino acid.

The method provides the VHH antibody having higher thermal stability than the VHH antibody represented by SEQ ID NO: 1. As above described, the VHH antibody has higher denaturation median temperature Tm than the VHH antibody represented by SEQ ID NO: 1.

EXAMPLES

Inventive Example 1: Screening of Thermostable VHH Antibody

The VHH antibodies of SEQ ID NO: 1 and SEQ ID NO: 12 were isolated as thermostable VHH antibodies from a phage library. The VHH antibodies of SEQ ID NO: 1 and SEQ ID NO: 12 had denaturation median temperature Tm of 51.2 and 60.3 degrees Celsius, respectively. To provide a VHH antibody having a higher thermal stability, the present inventors compared the sequences thereof with each other and consider amino acid substitution of SEQ ID NO: 1.

Inventive Example 2: Incorporation 1 of Amino Acid Substitution

The following four VHH antibodies were prepared.
(i) VHH antibody in which glycine in position 36 of SEQ ID NO: 1 was substituted with asparagine (SEQ ID NO: 3);
(ii) VHH antibody in which arginine in position 50 of SEQ ID NO: 1 was substituted with asparagine (SEQ ID NO: 4);
(iii) VHH antibody in which glycine in position 78 of SEQ ID NO: 1 was substituted with alanine (SEQ ID NO: 5); and
(iv) VHH antibody in which serine in position 116 of SEQ ID NO: 1 was substituted with arginine (SEQ ID NO: 6).

The present inventors amplified a polynucleotide with primers listed in Table 2, and then, transfected E. coli with a vector in which the amplified polynucleotide was incorporated to express these four VHH antibody. In Table 2, for example, the abbreviation "G36D" means substitution of glycine in position 36 with aspartic acid. The denaturation median temperature Tm of these four VHH antibodies was measured in accordance with the above-mentioned method. Table 3 shows difference (namely, ΔTm) between the denaturation median temperature Tm of SEQ ID NO: 3-SEQ ID NO: 6 and the denaturation median temperature Tm of SEQ ID NO: 1.

TABLE 2

| Primer | Sequence | | SEQ ID NO: |
| --- | --- | --- | --- |
| G36D | forward | CATGGGCTGGTTCCGCCAGGCTC | 13 |
| G36D | reverse | GCATAGTCACTAAAGGTGCGTCCAGAGGCTGC | 14 |
| R50L | forward | CTTGAGTTTGTAGCGCGTATAAACTGGAGTGGTACACTC | 15 |
| R50L | reverse | CTCCTTCCCTGGAGCCTGGCGG | 16 |
| G78A | forward | GCCTCCAGAGACAACGCCAAGAACAC | 17 |
| G78A | reverse | GGTGAATCGGCCCTTCACGGAGTC | 18 |
| S116R | forward | GTACTGGGGCCAGGGGACCCAG | 19 |
| S116R | reverse | CTATAGCCGGACGGATCGTAGTTACTACCACTGTC | 20 |

TABLE 3

| SEQ ID NO: | ΔTm (degrees Celsius) |
| --- | --- |
| 3 | +1.5 |
| 4 | +2.5 |
| 5 | +7.1 |
| 6 | −1.0 |

As is clear from Table 3, the VHH antibody in which any one of amino acid in position 36, 50, and 78 has been substituted has denaturation median temperature Tm of not less than 53.1 degrees Celsius. This means that the value of ΔTm is a positive value. The VHH antibody in which the amino acid in position 116 has been substituted has a negative value of ΔTm; however, has denaturation median temperature Tm of not less than 50 degrees Celsius.

Inventive Example 3: Incorporation 2 of Amino Acid Substitution

The following five VHH antibodies were prepared.
(i) VHH antibody in which glycine in position 36 and serine in position 116 of SEQ ID NO: 1 were substituted with asparagine and arginine, respectively (SEQ ID NO: 7);
(ii) VHH antibody in which arginine in position 50 and glycine in position 78 of SEQ ID NO: 1 were substituted with leucine and alanine, respectively (SEQ ID NO: 8);
(iii) VHH antibody in which glycine in position 36, arginine in position 50, and serine in position 116 of SEQ ID NO: 1 were substituted with asparagine, leucine, and arginine, respectively (SEQ ID NO: 9);
(iv) VHH antibody in which glycine in position 36, glycine in position 78, and serine in position 116 of SEQ ID NO: 1 were substituted with asparagine, alanine, and arginine, respectively (SEQ ID NO: 10); and
(v) VHH antibody in which glycine in position 36, arginine in position 50, glycine in position 78, and serine in position 116 of SEQ ID NO: 1 were substituted with asparagine, leucine, alanine, and arginine, respectively (SEQ ID NO: 11);

The denaturation median point temperature Tm of these VHH antibodies was measured in accordance with the above method. Table 4 shows the results thereof.

TABLE 4

| SEQ ID NO: | Tm (degrees Celsius) |
| --- | --- |
| 1 | 56.9 |
| 7 | 57.5 |
| 8 | 65.0 |
| 9 | 59.6 |
| 10 | 65.5 |
| 11 | 69.1 |

As is clear from Table 4, the substation of two or more amino acids improves the thermal stability more. The VHH antibody in which the four amino acids have been substituted has the highest denaturation median point temperature Tm.

Figure 2:
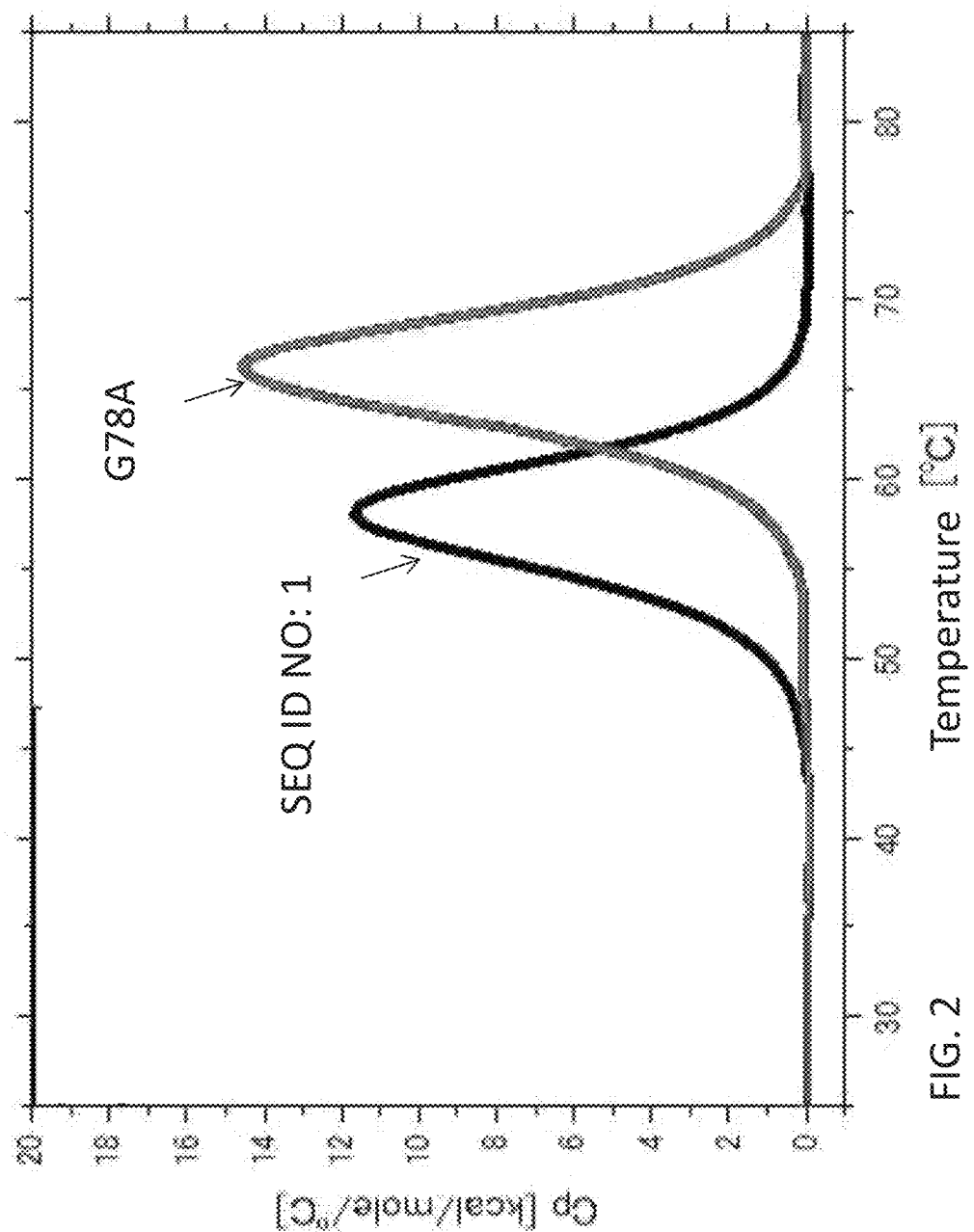
FIG. 2 is a graph showing comparison of thermostability of a VHH antibody in which one amino acid is substituted to thermostability of the VHH antibody of SEQ ID NO: 1.
Figure 3:
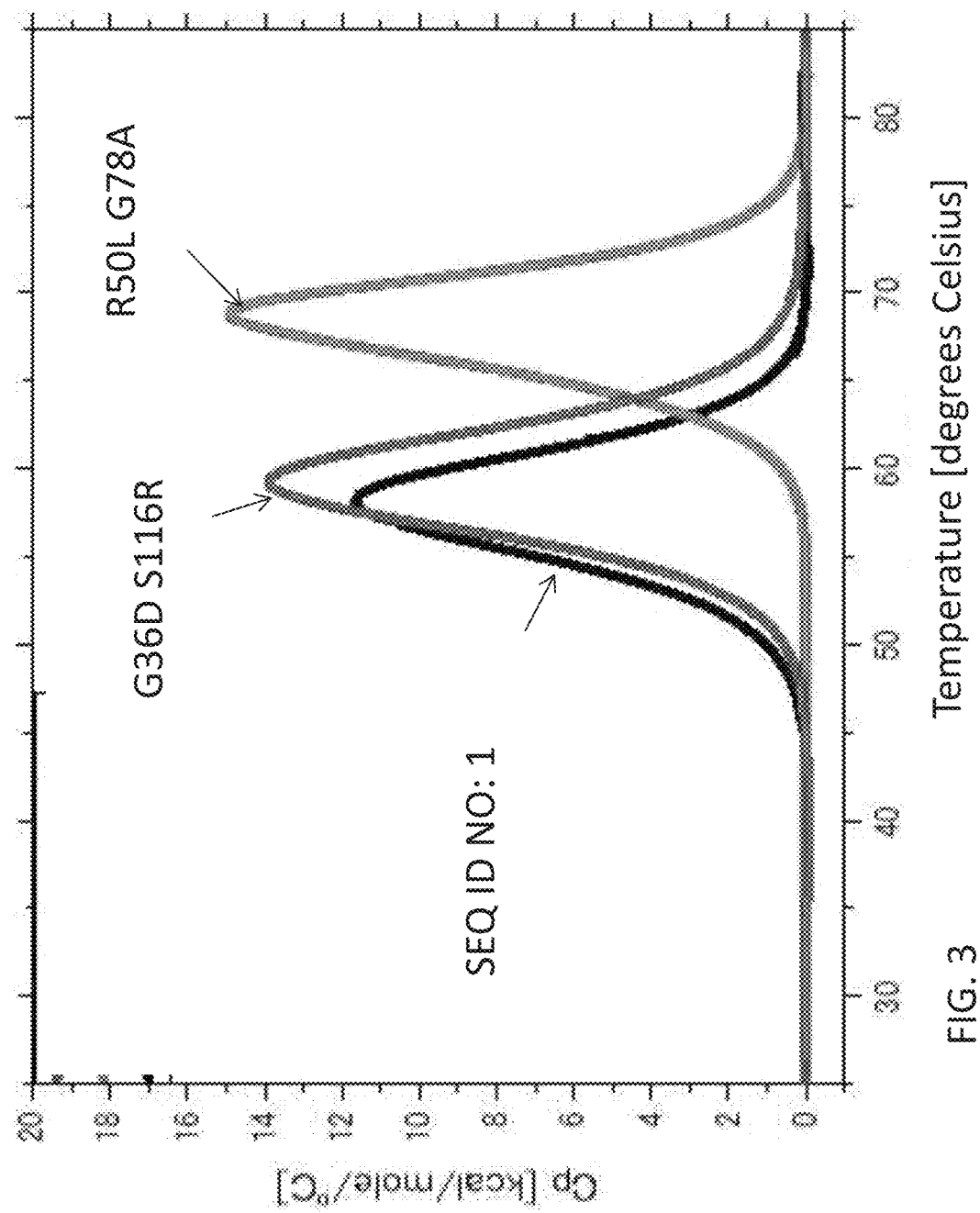
FIG. 3 is a graph showing comparison of thermostability of a VHH antibody in which two amino acids are substituted to thermostability of the VHH antibody of SEQ ID NO: 1.

FIG. 2 is a graph showing comparison of thermostability of the VHH antibody in which one amino acid is substituted to thermostability of the VHH antibody of SEQ ID NO: 1. FIG. 3 is a graph showing comparison of thermostability of the VHH antibody in which two amino acids are substituted to thermostability of the VHH antibody of SEQ ID NO: 1.

Inventive Example 4: Confirmation of Affinity of VHH Antibody

The binding affinity of the provided VHH antibodies to human serum albumin was measured with surface plasmon resonance. Table 5 shows the results thereof.

TABLE 5

| SEQ ID NO: | $k_{on}$ [1/M · s] | $k_{off}$ [1/s] | $K_D$ [M] |
| --- | --- | --- | --- |
| 1 | $1.42 \times 10^6$ | 0.371 | $2.61 \times 10^{-7}$ |
| 3 | $2.04 \times 10^6$ | 0.1254 | $6.14 \times 10^{-8}$ |
| 4 | $1.93 \times 10^6$ | 0.3029 | $1.57 \times 10^{-7}$ |
| 5 | $6.12 \times 10^4$ | 0.8061 | $1.32 \times 10^{-5}$ |
| 6 | $1.66 \times 10^7$ | 0.5906 | $3.56 \times 10^{-8}$ |
| 7 | $1.44 \times 10^6$ | 0.06431 | $4.47 \times 10^{-8}$ |
| 8 | $2.42 \times 10^4$ | 0.9503 | $3.92 \times 10^{-5}$ |
| 9 | $1.13 \times 10^6$ | 0.08793 | $7.79 \times 10^{-8}$ |
| 10 | $1.13 \times 10^6$ | 0.4108 | $3.65 \times 10^{-7}$ |
| 11 | $9.33 \times 10^5$ | 0.3547 | $3.80 \times 10^{-7}$ |

As is clear from Table 5, the VHH antibodies of SEQ ID NO: 3-SEQ ID NO: 11 in which the amino acid(s) was/were substituted exhibit the binding affinity which is equal to or more than that of the VHH antibody represented by SEQ ID NO: 1. In this way, the present inventors confirmed that the VHH antibodies of SEQ ID NO: 3-SEQ ID NO: 11 in which the amino acid(s) was/were substituted serve as an anti-human serum albumin VHH antibody.

INDUSTRIAL APPLICABILITY

The present disclosure provides a novel and thermostable VHH antibody.

SEQUENCE LISTING

<110> Panasonic Intellectual Property Management Co., Ltd.

<120> VHH antibody

<130> P1013355US01

<150> JP 2018-110552
<151> 2018 Jun. 8

<160> 20

<170> PatentIn version 3.5

SEQUENCE LISTING

```
<210> 1
<211> 124
<212> PRT
<213> Artificial Sequence

<220>
<223> WT VHH

<400> 1
Gln Val Gln Leu Val Glu Ser Gly Gly Gly Leu Val Gln Ala Gly Asp Ser
1               5                   10                  15
Leu Arg Leu Ser Cys Ala Ala Ser Gly Arg Thr Phe Ser Gly Tyr Ala Met
            20                  25                  30
Gly Trp Phe Arg Gln Ala Pro Gly Lys Glu Arg Glu Phe Val Ala Arg Ile
35                  40                  45                  50
Asn Trp Ser Gly Thr Leu Thr Tyr Tyr Ala Asp Ser Val Lys Gly Arg Phe
                55                  60                  65
Thr Gly Ser Arg Asp Asn Ala Lys Asn Thr Val Tyr Leu Gln Met Asn Ser
    70                  75                  80                  85
Leu Lys Pro Glu Asp Thr Ala Val Tyr Tyr Cys Ala Gln Arg Gly Asp Ser
                90                  95                  100
Gly Ser Asn Tyr Asp Pro Ser Gly Tyr Ser Tyr Trp Gly Gln Gly Thr Gln
                105                 110                 115
Val Thr Val Ser Ser
        120

<210> 2
<211> 372
<212> DNA
<213> Artificial Sequence

<220>
<223> WT VHH

<400> 2
caggtgcagc tcgtggagtc tgggggagga ttggtgcagg ctggggactc tctgagactc   60
tcctgtgcag cctctggacg cacctttagt ggctatgcca tgggctggtt ccgccaggct  120
ccagggaagg agcgtgagtt tgtagcgcgt ataaactgga gtggtacact cacatactat  180
gcagactccg tgaagggccg attcaccggc tccagagaca cgccaagaa cacagtgtat  240
ctgcaaatga acagcctgaa acctgaggac acggccgttt attactgtgc ccagagaggc  300
gacagtggta gtaactacga tccgtccggc tatagctact ggggccaggg gacccaggtc  360
accgtctcct ca                                                      372

<210> 3
<211> 124
<212> PRT
<213> Artificial Sequence

<220>
<223> G36D mutant

<400> 3
Gln Val Gln Leu Val Glu Ser Gly Gly Gly Leu Val Gln Ala Gly Asp Ser
1               5                   10                  15
Leu Arg Leu Ser Cys Ala Ala Ser Gly Arg Thr Phe Ser Asp Tyr Ala Met
            20                  25                  30
Gly Trp Phe Arg Gln Ala Pro Gly Lys Glu Arg Glu Phe Val Ala Arg Ile
35                  40                  45                  50
Asn Trp Ser Gly Thr Leu Thr Tyr Tyr Ala Asp Ser Val Lys Gly Arg Phe
                55                  60                  65
Thr Gly Ser Arg Asp Asn Ala Lys Asn Thr Val Tyr Leu Gln Met Asn Ser
    70                  75                  80                  85
Leu Lys Pro Glu Asp Thr Ala Val Tyr Tyr Cys Ala Gln Arg Gly Asp Ser
                90                  95                  100
Gly Ser Asn Tyr Asp Pro Ser Gly Tyr Ser Tyr Trp Gly Gln Gly Thr Gln
                105                 110                 115
Val Thr Val Ser Ser
        120

<210> 4
<211> 124
<212> PRT
<213> Artificial Sequence

<220>
<223> R50L mutant
```

SEQUENCE LISTING

```
<400> 4
Gln Val Gln Leu Val Glu Ser Gly Gly Gly Leu Val Gln Ala Gly Asp Ser
1               5                   10                  15
Leu Arg Leu Ser Cys Ala Ala Ser Gly Arg Thr Phe Ser Gly Tyr Ala Met
            20                  25                  30
Gly Trp Phe Arg Gln Ala Pro Gly Lys Glu Leu Glu Phe Val Ala Arg Ile
35                  40                  45                  50
Asn Trp Ser Gly Thr Leu Thr Tyr Tyr Ala Asp Ser Val Lys Gly Arg Phe
                55                  60                  65
Thr Gly Ser Arg Asp Asn Ala Lys Asn Thr Val Tyr Leu Gln Met Asn Ser
    70                  75                  80                  85
Leu Lys Pro Glu Asp Thr Ala Val Tyr Tyr Cys Ala Gln Arg Gly Asp Ser
                90                  95                  100
Gly Ser Asn Tyr Asp Pro Ser Gly Tyr Ser Tyr Trp Gly Gln Gly Thr Gln
            105                 110                 115
Val Thr Val Ser Ser
            120

<210> 5
<211> 124
<212> PRT
<213> Artificial Sequence

<220>
<223> G78A mutant

<400> 5
Gln Val Gln Leu Val Glu Ser Gly Gly Gly Leu Val Gln Ala Gly Asp Ser
1               5                   10                  15
Leu Arg Leu Ser Cys Ala Ala Ser Gly Arg Thr Phe Ser Gly Tyr Ala Met
            20                  25                  30
Gly Trp Phe Arg Gln Ala Pro Gly Lys Glu Arg Glu Phe Val Ala Arg Ile
35                  40                  45                  50
Asn Trp Ser Gly Thr Leu Thr Tyr Tyr Ala Asp Ser Val Lys Gly Arg Phe
                55                  60                  65
Thr Ala Ser Arg Asp Asn Ala Lys Asn Thr Val Tyr Leu Gln Met Asn Ser
    70                  75                  80                  85
Leu Lys Pro Glu Asp Thr Ala Val Tyr Tyr Cys Ala Gln Arg Gly Asp Ser
                90                  95                  100
Gly Ser Asn Tyr Asp Pro Ser Gly Tyr Ser Tyr Trp Gly Gln Gly Thr Gln
            105                 110                 115
Val Thr Val Ser Ser
            120

<210> 6
<211> 124
<212> PRT
<213> Artificial Sequence

<220>
<223> S116R mutant

<400> 6
Gln Val Gln Leu Val Glu Ser Gly Gly Gly Leu Val Gln Ala Gly Asp Ser
1               5                   10                  15
Leu Arg Leu Ser Cys Ala Ala Ser Gly Arg Thr Phe Ser Gly Tyr Ala Met
            20                  25                  30
Gly Trp Phe Arg Gln Ala Pro Gly Lys Glu Arg Glu Phe Val Ala Arg Ile
35                  40                  45                  50
Asn Trp Ser Gly Thr Leu Thr Tyr Tyr Ala Asp Ser Val Lys Gly Arg Phe
                55                  60                  65
Thr Gly Ser Arg Asp Asn Ala Lys Asn Thr Val Tyr Leu Gln Met Asn Ser
    70                  75                  80                  85
Leu Lys Pro Glu Asp Thr Ala Val Tyr Tyr Cys Ala Gln Arg Gly Asp Ser
                90                  95                  100
Gly Ser Asn Tyr Asp Pro Ser Gly Tyr Arg Tyr Trp Gly Gln Gly Thr Gln
            105                 110                 115
Val Thr Val Ser Ser
            120

<210> 7
<211> 124
<212> PRT
<213> Artificial Sequence

<220>
<223> G36D/S116R mutant
```

```
<400> 7
Gln Val Gln Leu Val Glu Ser Gly Gly Gly Leu Val Gln Ala Gly Asp Ser
1               5                   10                  15
Leu Arg Leu Ser Cys Ala Ala Ser Gly Arg Thr Phe Ser Asp Tyr Ala Met
            20                  25                  30
Gly Trp Phe Arg Gln Ala Pro Gly Lys Glu Arg Glu Phe Val Ala Arg Ile
35                  40                  45                  50
Asn Trp Ser Gly Thr Leu Thr Tyr Tyr Ala Asp Ser Val Lys Gly Arg Phe
                55                  60                  65
Thr Gly Ser Arg Asp Asn Ala Lys Asn Thr Val Tyr Leu Gln Met Asn Ser
    70                  75                  80                  85
Leu Lys Pro Glu Asp Thr Ala Val Tyr Tyr Cys Ala Gln Arg Gly Asp Ser
                90                  95                  100
Gly Ser Asn Tyr Asp Pro Ser Gly Tyr Arg Tyr Trp Gly Gln Gly Thr Gln
            105                 110                 115
Val Thr Val Ser Ser
            120

<210> 8
<211> 124
<212> PRT
<213> Artificial Sequence

<220>
<223> R50L/G78A mutant

<400> 8
Gln Val Gln Leu Val Glu Ser Gly Gly Gly Leu Val Gln Ala Gly Asp Ser
1               5                   10                  15
Leu Arg Leu Ser Cys Ala Ala Ser Gly Arg Thr Phe Ser Gly Tyr Ala Met
            20                  25                  30
Gly Trp Phe Arg Gln Ala Pro Gly Lys Glu Leu Glu Phe Val Ala Arg Ile
35                  40                  45                  50
Asn Trp Ser Gly Thr Leu Thr Tyr Tyr Ala Asp Ser Val Lys Gly Arg Phe
                55                  60                  65
Thr Ala Ser Arg Asp Asn Ala Lys Asn Thr Val Tyr Leu Gln Met Asn Ser
    70                  75                  80                  85
Leu Lys Pro Glu Asp Thr Ala Val Tyr Tyr Cys Ala Gln Arg Gly Asp Ser
                90                  95                  100
Gly Ser Asn Tyr Asp Pro Ser Gly Tyr Ser Tyr Trp Gly Gln Gly Thr Gln
            105                 110                 115
Val Thr Val Ser Ser
            120

<210> 9
<211> 124
<212> PRT
<213> Artificial Sequence

<220>
<223> G36D/R50L/S116R mutant

<400> 9
Gln Val Gln Leu Val Glu Ser Gly Gly Gly Leu Val Gln Ala Gly Asp Ser
1               5                   10                  15
Leu Arg Leu Ser Cys Ala Ala Ser Gly Arg Thr Phe Ser Asp Tyr Ala Met
            20                  25                  30
Gly Trp Phe Arg Gln Ala Pro Gly Lys Glu Leu Glu Phe Val Ala Arg Ile
35                  40                  45                  50
Asn Trp Ser Gly Thr Leu Thr Tyr Tyr Ala Asp Ser Val Lys Gly Arg Phe
                55                  60                  65
Thr Gly Ser Arg Asp Asn Ala Lys Asn Thr Val Tyr Leu Gln Met Asn Ser
    70                  75                  80                  85
Leu Lys Pro Glu Asp Thr Ala Val Tyr Tyr Cys Ala Gln Arg Gly Asp Ser
                90                  95                  100
Gly Ser Asn Tyr Asp Pro Ser Gly Tyr Arg Tyr Trp Gly Gln Gly Thr Gln
            105                 110                 115
Val Thr Val Ser Ser
            120

<210> 10
<211> 124
<212> PRT
<213> Artificial Sequence

<220>
```

SEQUENCE LISTING

<223> G36D/G78A/S116R mutant

<400> 10

```
Gln Val Gln Leu Val Glu Ser Gly Gly Gly Leu Val Gln Ala Gly Asp Ser
1               5                   10                  15
Leu Arg Leu Ser Cys Ala Ala Ser Gly Arg Thr Phe Ser Asp Tyr Ala Met
            20                  25                  30
Gly Trp Phe Arg Gln Ala Pro Gly Lys Glu Arg Glu Phe Val Ala Arg Ile
35                      40                  45                  50
Asn Trp Ser Gly Thr Leu Thr Tyr Tyr Ala Asp Ser Val Lys Gly Arg Phe
                55                  60                  65
Thr Ala Ser Arg Asp Asn Ala Lys Asn Thr Val Tyr Leu Gln Met Asn Ser
        70                  75                  80                  85
Leu Lys Pro Glu Asp Thr Ala Val Tyr Tyr Cys Ala Gln Arg Gly Asp Ser
                    90                  95                  100
Gly Ser Asn Tyr Asp Pro Ser Gly Tyr Arg Tyr Trp Gly Gln Gly Thr Gln
            105                 110                 115
Val Thr Val Ser Ser
            120
```

<210> 11
<211> 124
<212> PRT
<213> Artificial Sequence

<220>
<223> G36D/R50L/G78A/S116R mutant

<400> 11

```
Gln Val Gln Leu Val Glu Ser Gly Gly Gly Leu Val Gln Ala Gly Asp Ser
1               5                   10                  15
Leu Arg Leu Ser Cys Ala Ala Ser Gly Arg Thr Phe Ser Asp Tyr Ala Met
            20                  25                  30
Gly Trp Phe Arg Gln Ala Pro Gly Lys Glu Leu Glu Phe Val Ala Arg Ile
35                      40                  45                  50
Asn Trp Ser Gly Thr Leu Thr Tyr Tyr Ala Asp Ser Val Lys Gly Arg Phe
                55                  60                  65
Thr Ala Ser Arg Asp Asn Ala Lys Asn Thr Val Tyr Leu Gln Met Asn Ser
        70                  75                  80                  85
Leu Lys Pro Glu Asp Thr Ala Val Tyr Tyr Cys Ala Gln Arg Gly Asp Ser
                    90                  95                  100
Gly Ser Asn Tyr Asp Pro Ser Gly Tyr Arg Tyr Trp Gly Gln Gly Thr Gln
            105                 110                 115
Val Thr Val Ser Ser
            120
```

<210> 12
<211> 124
<212> PRT
<213> Artificial Sequence

<220>
<223> WT VHH

<400> 12

```
Gln Leu Gln Leu Val Glu Ser Gly Gly Gly Leu Val Gln Ala Gly Asp Ser
1               5                   10                  15
Leu Arg Leu Ser Cys Ala Ala Ser Gly Arg Thr Phe Ser Asp Tyr Ala Met
            20                  25                  30
Gly Trp Phe Arg Gln Ala Pro Gly Lys Glu Leu Glu Phe Val Ala Arg Val
35                      40                  45                  50
Asn Trp Ser Gly Leu Leu Thr Tyr Tyr Ala Asp Ser Val Lys Gly Arg Phe
                55                  60                  65
Thr Ala Ser Arg Asp Asn Ala Lys Ser Thr Val Tyr Leu Gln Met Asn Ser
        70                  75                  80                  85
Leu Lys Pro Glu Asp Thr Ala Val Tyr Tyr Cys Ala Gln Arg Gly Asp Ser
                    90                  95                  100
Gly Ser Asn Phe Asp Pro Ser Gly Tyr Arg Tyr Trp Gly Gln Gly Thr Gln
            105                 110                 115
Val Thr Val Ser Ser
            120
```

<210> 13
<211> 23
<212> DNA
<213> Artificial Sequence

SEQUENCE LISTING

<220>
<223> G36D forward primer

<400> 13
catgggctgg ttccgccagg ctc                                        23

<210> 14
<211> 32
<212> DNA
<213> Artificial Sequence

<220>
<223> G36D reverse primer

<400> 14
gcatagtcac taaaggtgcg tccagaggct gc                              32

<210> 15
<211> 39
<212> DNA
<213> Artificial Sequence

<220>
<223> R50L forward primer

<400> 15
cttgagtttg tagcgcgtat aaactggagt ggtacactc                       39

<210> 16
<211> 22
<212> DNA
<213> Artificial Sequence

<220>
<223> R50L reverse primer

<400> 16
ctccttccct ggagcctggc gg                                         22

<210> 17
<211> 26
<212> DNA
<213> Artificial Sequence

<220>
<223> G78A forward primer

<400> 17
gcctccagag acaacgccaa gaacac                                     26

<210> 18
<211> 24
<212> DNA
<213> Artificial Sequence

<220>
<223> G78A reverse primer

<400> 18
ggtgaatcgg cccttcacgg agtc                                       24

<210> 19
<211> 22
<212> DNA
<213> Artificial Sequence

<220>
<223> S116R forward primer

<400> 19
gtactggggc caggggaccc ag                                         22

<210> 20
<211> 35
<212> DNA
<213> Artificial Sequence

SEQUENCE LISTING

<220>
<223> S116R reverse primer

<400> 20
ctatagccgg acggatcgta gttactacca ctgtc        35

SEQUENCE LISTING

<160> NUMBER OF SEQ ID NOS: 20

<210> SEQ ID NO 1
<211> LENGTH: 124
<212> TYPE: PRT
<213> ORGANISM: Artificial Sequence
<220> FEATURE:
<223> OTHER INFORMATION: WT VHH

<400> SEQUENCE: 1

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Gly Tyr
            20                  25                  30

Ala Met Gly Trp Phe Arg Gln Ala Pro Gly Lys Glu Arg Glu Phe Val
        35                  40                  45

Ala Arg Ile Asn Trp Ser Gly Thr Leu Thr Tyr Tyr Ala Asp Ser Val
    50                  55                  60

Lys Gly Arg Phe Thr Gly Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gln Arg Gly Asp Ser Gly Ser Asn Tyr Asp Pro Ser Gly Tyr Ser
            100                 105                 110

Tyr Trp Gly Gln Gly Thr Gln Val Thr Val Ser Ser
        115                 120

<210> SEQ ID NO 2
<211> LENGTH: 372
<212> TYPE: DNA
<213> ORGANISM: Artificial Sequence
<220> FEATURE:
<223> OTHER INFORMATION: WT VHH

<400> SEQUENCE: 2
caggtgcagc tcgtggagtc tgggggagga ttggtgcagg ctggggactc tctgagactc        60
tcctgtgcag cctctggacg caccttagt ggctatgcca tgggctggtt ccgccaggct       120
ccagggaagg agcgtgagtt tgtagcgcgt ataaactgga gtggtacact cacatactat       180
gcagactccg tgaagggccg attcaccggc tccagagaca acgccaagaa cacagtgtat       240
ctgcaaatga acagcctgaa acctgaggac acggccgttt attactgtgc ccagagaggc       300
gacagtggta gtaactacga tccgtccggc tatagctact ggggccaggg gacccaggtc       360
accgtctcct ca                                                          372

<210> SEQ ID NO 3
<211> LENGTH: 124
<212> TYPE: PRT
<213> ORGANISM: Artificial Sequence
<220> FEATURE:

<223> OTHER INFORMATION: G36D mutant

<400> SEQUENCE: 3

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Asp Tyr
            20                  25                  30

Ala Met Gly Trp Phe Arg Gln Ala Pro Gly Lys Glu Arg Glu Phe Val
        35                  40                  45

Ala Arg Ile Asn Trp Ser Gly Thr Leu Thr Tyr Tyr Ala Asp Ser Val
    50                  55                  60

Lys Gly Arg Phe Thr Gly Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gln Arg Gly Asp Ser Gly Ser Asn Tyr Asp Pro Ser Gly Tyr Ser
            100                 105                 110

Tyr Trp Gly Gln Gly Thr Gln Val Thr Val Ser Ser
            115                 120

<210> SEQ ID NO 4
<211> LENGTH: 124
<212> TYPE: PRT
<213> ORGANISM: Artificial Sequence
<220> FEATURE:
<223> OTHER INFORMATION: R50L mutant

<400> SEQUENCE: 4

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Gly Tyr
            20                  25                  30

Ala Met Gly Trp Phe Arg Gln Ala Pro Gly Lys Glu Leu Glu Phe Val
        35                  40                  45

Ala Arg Ile Asn Trp Ser Gly Thr Leu Thr Tyr Tyr Ala Asp Ser Val
    50                  55                  60

Lys Gly Arg Phe Thr Gly Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gln Arg Gly Asp Ser Gly Ser Asn Tyr Asp Pro Ser Gly Tyr Ser
            100                 105                 110

Tyr Trp Gly Gln Gly Thr Gln Val Thr Val Ser Ser
            115                 120

<210> SEQ ID NO 5
<211> LENGTH: 124
<212> TYPE: PRT
<213> ORGANISM: Artificial Sequence
<220> FEATURE:
<223> OTHER INFORMATION: G78A mutant

<400> SEQUENCE: 5

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Gly Tyr
            20                  25                  30

Ala Met Gly Trp Phe Arg Gln Ala Pro Gly Lys Glu Arg Glu Phe Val

```
            35                  40                  45

Ala Arg Ile Asn Trp Ser Gly Thr Leu Thr Tyr Tyr Ala Asp Ser Val
 50                  55                  60

Lys Gly Arg Phe Thr Ala Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Gln Arg Gly Asp Ser Gly Ser Asn Tyr Asp Pro Ser Gly Tyr Ser
                100                 105                 110

Tyr Trp Gly Gln Gly Thr Gln Val Thr Val Ser Ser
            115                 120

<210> SEQ ID NO 6
<211> LENGTH: 124
<212> TYPE: PRT
<213> ORGANISM: Artificial Sequence
<220> FEATURE:
<223> OTHER INFORMATION: S116R mutant

<400> SEQUENCE: 6

Gln Val Gln Leu Val Glu Ser Gly Gly Gly Leu Val Gln Ala Gly Asp
  1               5                  10                  15

Ser Leu Arg Leu Ser Cys Ala Ala Ser Gly Arg Thr Phe Ser Gly Tyr
                 20                  25                  30

Ala Met Gly Trp Phe Arg Gln Ala Pro Gly Lys Glu Arg Glu Phe Val
            35                  40                  45

Ala Arg Ile Asn Trp Ser Gly Thr Leu Thr Tyr Tyr Ala Asp Ser Val
 50                  55                  60

Lys Gly Arg Phe Thr Gly Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Gln Arg Gly Asp Ser Gly Ser Asn Tyr Asp Pro Ser Gly Tyr Arg
                100                 105                 110

Tyr Trp Gly Gln Gly Thr Gln Val Thr Val Ser Ser
            115                 120

<210> SEQ ID NO 7
<211> LENGTH: 124
<212> TYPE: PRT
<213> ORGANISM: Artificial Sequence
<220> FEATURE:
<223> OTHER INFORMATION: G36D/S116R mutant

<400> SEQUENCE: 7

Gln Val Gln Leu Val Glu Ser Gly Gly Gly Leu Val Gln Ala Gly Asp
  1               5                  10                  15

Ser Leu Arg Leu Ser Cys Ala Ala Ser Gly Arg Thr Phe Ser Asp Tyr
                 20                  25                  30

Ala Met Gly Trp Phe Arg Gln Ala Pro Gly Lys Glu Arg Glu Phe Val
            35                  40                  45

Ala Arg Ile Asn Trp Ser Gly Thr Leu Thr Tyr Tyr Ala Asp Ser Val
 50                  55                  60

Lys Gly Arg Phe Thr Gly Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95
```

Ala Gln Arg Gly Asp Ser Gly Ser Asn Tyr Asp Pro Ser Gly Tyr Arg
            100                 105                 110

Tyr Trp Gly Gln Gly Thr Gln Val Thr Val Ser Ser
            115                 120

<210> SEQ ID NO 8
<211> LENGTH: 124
<212> TYPE: PRT
<213> ORGANISM: Artificial Sequence
<220> FEATURE:
<223> OTHER INFORMATION: R50L/G78A mutant

<400> SEQUENCE: 8

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Gly Tyr
            20                  25                  30

Ala Met Gly Trp Phe Arg Gln Ala Pro Gly Lys Glu Leu Glu Phe Val
        35                  40                  45

Ala Arg Ile Asn Trp Ser Gly Thr Leu Thr Tyr Tyr Ala Asp Ser Val
    50                  55                  60

Lys Gly Arg Phe Thr Ala Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gln Arg Gly Asp Ser Gly Ser Asn Tyr Asp Pro Ser Gly Tyr Ser
            100                 105                 110

Tyr Trp Gly Gln Gly Thr Gln Val Thr Val Ser Ser
            115                 120

<210> SEQ ID NO 9
<211> LENGTH: 124
<212> TYPE: PRT
<213> ORGANISM: Artificial Sequence
<220> FEATURE:
<223> OTHER INFORMATION: G36D/R50L/S116R mutant

<400> SEQUENCE: 9

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Asp Tyr
            20                  25                  30

Ala Met Gly Trp Phe Arg Gln Ala Pro Gly Lys Glu Leu Glu Phe Val
        35                  40                  45

Ala Arg Ile Asn Trp Ser Gly Thr Leu Thr Tyr Tyr Ala Asp Ser Val
    50                  55                  60

Lys Gly Arg Phe Thr Gly Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gln Arg Gly Asp Ser Gly Ser Asn Tyr Asp Pro Ser Gly Tyr Arg
            100                 105                 110

Tyr Trp Gly Gln Gly Thr Gln Val Thr Val Ser Ser
            115                 120

<210> SEQ ID NO 10
<211> LENGTH: 124
<212> TYPE: PRT
<213> ORGANISM: Artificial Sequence
<220> FEATURE:
<223> OTHER INFORMATION: G36D/G78A/S116R mutant

<400> SEQUENCE: 10

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Asp Tyr
            20                  25                  30

Ala Met Gly Trp Phe Arg Gln Ala Pro Gly Lys Glu Arg Glu Phe Val
        35                  40                  45

Ala Arg Ile Asn Trp Ser Gly Thr Leu Thr Tyr Tyr Ala Asp Ser Val
    50                  55                  60

Lys Gly Arg Phe Thr Ala Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gln Arg Gly Asp Ser Gly Ser Asn Tyr Asp Pro Ser Gly Tyr Arg
            100                 105                 110

Tyr Trp Gly Gln Gly Thr Gln Val Thr Val Ser Ser
        115                 120

<210> SEQ ID NO 11
<211> LENGTH: 124
<212> TYPE: PRT
<213> ORGANISM: Artificial Sequence
<220> FEATURE:
<223> OTHER INFORMATION: G36D/R50L/G78A/S116R mutant

<400> SEQUENCE: 11

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Asp Tyr
            20                  25                  30

Ala Met Gly Trp Phe Arg Gln Ala Pro Gly Lys Glu Leu Glu Phe Val
        35                  40                  45

Ala Arg Ile Asn Trp Ser Gly Thr Leu Thr Tyr Tyr Ala Asp Ser Val
    50                  55                  60

Lys Gly Arg Phe Thr Ala Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gln Arg Gly Asp Ser Gly Ser Asn Tyr Asp Pro Ser Gly Tyr Arg
            100                 105                 110

Tyr Trp Gly Gln Gly Thr Gln Val Thr Val Ser Ser
        115                 120

<210> SEQ ID NO 12
<211> LENGTH: 124
<212> TYPE: PRT
<213> ORGANISM: Artificial Sequence
<220> FEATURE:
<223> OTHER INFORMATION: WT VHH

<400> SEQUENCE: 12

Gln Leu Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Asp Tyr
            20                  25                  30

-continued

Ala Met Gly Trp Phe Arg Gln Ala Pro Gly Lys Glu Leu Glu Phe Val
         35                  40                  45

Ala Arg Val Asn Trp Ser Gly Leu Leu Thr Tyr Tyr Ala Asp Ser Val
 50                  55                  60

Lys Gly Arg Phe Thr Ala Ser Arg Asp Asn Ala Lys Ser Thr Val Tyr
 65                  70                  75                  80

Leu Gln Met Asn Ser Leu Lys Pro Glu Asp Thr Ala Val Tyr Tyr Cys
             85                  90                  95

Ala Gln Arg Gly Asp Ser Gly Ser Asn Phe Asp Pro Ser Gly Tyr Arg
            100                 105                 110

Tyr Trp Gly Gln Gly Thr Gln Val Thr Val Ser Ser
        115                 120

<210> SEQ ID NO 13
<211> LENGTH: 23
<212> TYPE: DNA
<213> ORGANISM: Artificial Sequence
<220> FEATURE:
<223> OTHER INFORMATION: G36D forward primer

<400> SEQUENCE: 13
catgggctgg ttccgccagg ctc                                        23

<210> SEQ ID NO 14
<211> LENGTH: 32
<212> TYPE: DNA
<213> ORGANISM: Artificial Sequence
<220> FEATURE:
<223> OTHER INFORMATION: G36D reverse primer

<400> SEQUENCE: 14
gcatagtcac taaaggtgcg tccagaggct gc                              32

<210> SEQ ID NO 15
<211> LENGTH: 39
<212> TYPE: DNA
<213> ORGANISM: Artificial Sequence
<220> FEATURE:
<223> OTHER INFORMATION: R50L forward primer

<400> SEQUENCE: 15
cttgagtttg tagcgcgtat aaactggagt ggtacactc                       39

<210> SEQ ID NO 16
<211> LENGTH: 22
<212> TYPE: DNA
<213> ORGANISM: Artificial Sequence
<220> FEATURE:
<223> OTHER INFORMATION: R50L reverse primer

<400> SEQUENCE: 16
ctccttccct ggagcctggc gg                                         22

<210> SEQ ID NO 17
<211> LENGTH: 26
<212> TYPE: DNA
<213> ORGANISM: Artificial Sequence
<220> FEATURE:
<223> OTHER INFORMATION: G78A forward primer

<400> SEQUENCE: 17
gcctccagag acaacgccaa gaacac                                     26

```
<210> SEQ ID NO 18
<211> LENGTH: 24
<212> TYPE: DNA
<213> ORGANISM: Artificial Sequence
<220> FEATURE:
<223> OTHER INFORMATION: G78A reverse primer

<400> SEQUENCE: 18
ggtgaatcgg cccttcacgg agtc                                            24

<210> SEQ ID NO 19
<211> LENGTH: 22
<212> TYPE: DNA
<213> ORGANISM: Artificial Sequence
<220> FEATURE:
<223> OTHER INFORMATION: S116R forward primer

<400> SEQUENCE: 19
gtactggggc caggggaccc ag                                              22

<210> SEQ ID NO 20
<211> LENGTH: 35
<212> TYPE: DNA
<213> ORGANISM: Artificial Sequence
<220> FEATURE:
<223> OTHER INFORMATION: S116R reverse primer

<400> SEQUENCE: 20
ctatagccgg acggatcgta gttactacca ctgtc                                35
```

The invention claimed is:

1. A VHH antibody including an amino acid sequence represented by any one selected from the group consisting of SEQ ID NO: 3-SEQ ID NO: 12.

* * * * *